US012565463B2

(12) United States Patent
Paterson et al.

(10) Patent No.: US 12,565,463 B2
(45) Date of Patent: Mar. 3, 2026

(54) FISCHER-TROPSCH PROCESSES PRODUCING INCREASED AMOUNTS OF ALCOHOLS

(71) Applicant: BP P.L.C., London (GB)

(72) Inventors: Alexander James Paterson, Yorkshire (GB); John Glenn Sunley, Yorkshire (GB)

(73) Assignee: BP P.L.C., London (GB)

( * ) Notice: Subject to any disclaimer, the term of this patent is extended or adjusted under 35 U.S.C. 154(b) by 386 days.

(21) Appl. No.: 18/252,683

(22) PCT Filed: Dec. 17, 2021

(86) PCT No.: PCT/IB2021/061974
§ 371 (c)(1),
(2) Date: May 11, 2023

(87) PCT Pub. No.: WO2022/130343
PCT Pub. Date: Jun. 23, 2022

(65) Prior Publication Data
US 2024/0002317 A1     Jan. 4, 2024

(30) Foreign Application Priority Data
Dec. 18, 2020     (EP) .................................... 20215767

(51) Int. Cl.
| | |
|---|---|
| *C07C 29/156* | (2006.01) |
| *B01J 35/45* | (2024.01) |
| *C07C 29/151* | (2006.01) |

(52) U.S. Cl.
CPC ............. *C07C 29/156* (2013.01); *B01J 35/45* (2024.01); *C07C 29/1512* (2013.01)

(58) Field of Classification Search
CPC ..... B01J 23/8892; B01J 35/45; C07C 29/156; C07C 29/1512; C10G 2/332
See application file for complete search history.

(56) References Cited

U.S. PATENT DOCUMENTS 5,409,877 A     4/1995  Takeuchi et al.

FOREIGN PATENT DOCUMENTS

WO     2019/154885 A1     8/2019

OTHER PUBLICATIONS

Paterson James et al., "Manipulation of Fischer-Tropsch Synthesis for Production of Higher Alcohols Using Manganese Promoters", Chemcatchem, vol. 10, No. 22, Nov. 22, 2018, pp. 5154-5163.
Paterson James et al., "Elucidating the Role of Bifunctional Cobalt-Manganese Catalyst Interactions for Higher Alcohol Synthesis", European Journal of Inorganic Chemistry, vol. 2020, No. 24, Jun. 30, 2020, pp. 2312-2324.
International Search Report and Written Opinion for PCT/IB2021/061974, 12 pages, mailed Feb. 22, 2022.
Extended European Search Report for EP 20215767.3, 8 pages, mailed Jun. 9, 2021.
Barrett Elliott et al, "The Determination of Pore vol. and Area Distributions in Porous Substances. I. Computations from Nitrogren Isotherms", J Am Chem. Soc., vol. 73, Jan. 1951, pp. 373-380.
Brunauer S et al., "Adsportion of Gases in Multimolecular Layers", J. Amer. Chem. Soc. 60, 309 (1938).

*Primary Examiner* — Jafar F Parsa
(74) *Attorney, Agent, or Firm* — McDonnell Boehnen Hulbert & Berghoff LLP

(57) ABSTRACT

The present disclosure relates generally to compositions and processes for producing Fischer-Tropsch catalysts. In particular, the disclosure provides for a process for producing a product composition comprising alcohols and liquid hydrocarbons via a Fischer-Tropsch synthesis reaction, the process comprising: contacting a mixture of hydrogen and a gaseous carbon oxide that is carbon monoxide, carbon dioxide or a combination thereof and an olefin co-feed with a supported cobalt-manganese Fischer-Tropsch synthesis catalyst to provide the product composition; wherein the olefin co-feed comprises at least one $C_2$-$C_{14}$ olefin and is present in an amount in the range of 0.001 wt % to 40 wt % relative to the total amount of hydrogen, the gaseous carbon oxide and olefin; wherein a weight ratio of manganese to cobalt in the catalyst is at least 0.05 on an elemental basis.

20 Claims, No Drawings

FISCHER-TROPSCH PROCESSES PRODUCING INCREASED AMOUNTS OF ALCOHOLS

This application is a national stage application under 35 U.S.C. § 371 of International Application No. PCT/IB2021/061974, filed Dec. 17, 2021, which claims priority to EP Application Serial No. 20215767.3, filed Dec. 18, 2020, incorporated by reference herein in their entirety.

BACKGROUND OF THE DISCLOSURE

Field

The present disclosure relates to Fischer-Tropsch processes for the production of products having increased amounts of alcohols from a mixture of hydrogen and carbon monoxide and/or carbon dioxide gases.

Technical Background

The conversion of synthesis gas into hydrocarbons by the Fischer-Tropsch process has been known for many years. The growing importance of alternative energy sources has resulted in renewed interest in the Fischer-Tropsch (FT) process as it allows a direct and environmentally acceptable route to high-quality fuels and feedstock chemicals through use of bio-derived carbon sources.

FT processes are known to typically produce linear hydrocarbons for use in fuels, as well as oxygenates which serve as valuable feedstock chemicals. The hydrocarbon fuel deriving from FT processes is better able to meet increasingly stringent environmental regulations compared to conventional refinery-produced fuels, as FT-derived fuels typically have lower contents of sulfur, nitrogen, and aromatic compounds which contribute to the emission of potent pollutants such as $SO_2$, $NO_x$, and particulates. Alcohols derived from FT processes often have a higher octane rating than hydrocarbons and thus burn more completely, thereby reducing the environmental impact of such a fuel. Alcohols and other oxygenates obtained may also be used as reagents in other processes, such as in the synthesis of lubricants.

A variety of transition metals have been identified to be catalytically active in the conversion of synthesis gas into hydrocarbons and oxygenated derivatives thereof. In particular, cobalt, nickel, and iron have been studied, often in combination with a support material, of which the most common are alumina, silica and carbon.

Typically, the principal focus in producing Fischer-Tropsch synthesis catalysts is for improving activity and selectivity for $C_{5+}$ hydrocarbons (e.g., paraffins). While they are industrially-important products in their own right, alcohols are typically produced merely as a side product of Fischer-Tropsch processes, in much lower yield.

Accordingly, there exists a need to improve the activity and selectivity of a Fischer-Tropsch process for the production of alcohols in increased amounts.

SUMMARY

The inventors have found a process to form selectively produce high levels of olefins and alcohols in a Fischer-Tropsch synthesis reaction.

Accordingly, one aspect of the disclosure provides for a process for converting a mixture of hydrogen and a gaseous carbon oxide that is carbon monoxide, carbon dioxide or a combination thereof to a product composition comprising alcohols and liquid hydrocarbons via a Fischer-Tropsch synthesis reaction, the process comprising:

contacting a mixture of hydrogen and the gaseous carbon oxide (e.g., in the form of a synthesis gas mixture) and an olefin co-feed with a supported cobalt-manganese Fischer-Tropsch synthesis catalyst to provide the product composition;

wherein the olefin co-feed comprises at least one $C_2$-$C_{14}$ olefin and is present in an amount in the range of 0.001 wt % to 40 wt % relative to the total amount of hydrogen, the gaseous carbon oxide and olefin;

wherein a weight ratio of manganese to cobalt in the catalyst is at least 0.05 on an elemental basis; and wherein the molar ratio of hydrogen to the gaseous carbon oxide in the mixture of hydrogen and the gaseous carbon oxide is at least 0.5.

Other aspects of the disclosure will be apparent to those skilled in the art in view of the description that follows.

DETAILED DESCRIPTION

The present disclosure is concerned with processes to increase alcohol selectivity in a Fischer-Tropsch process. As described in International Patent Application Publication no. 2019/154885 and in James Paterson et al, "Manipulation of Fischer-Tropsch Synthesis for Production of Higher Alcohols Using Manganese Promoters," ChemCatChem, 10(22), 5154-5163 (2018), each of which is hereby incorporated herein by reference in its entirety, the use of catalysts including manganese can provide somewhat increased amounts of alcohol in the product stream. The inventors have now found that the use of an olefin co-feed in the Fischer-Tropsch reaction (i.e., along with a gaseous carbon oxide and hydrogen) advantageously results in increased alcohol selectivity, as evidenced by the Examples below. Surprisingly, the increase in alcohol yield can be in excess of the amount of olefin added.

Accordingly, one aspect of the disclosure provides for a process for converting a mixture of hydrogen and a gaseous carbon oxide to a product composition comprising alcohols and liquid hydrocarbons via a Fischer-Tropsch synthesis reaction, the process comprising:

contacting a mixture of hydrogen and a gaseous carbon oxide that is carbon monoxide, carbon dioxide or a combination thereof (e.g., in the form of a synthesis gas mixture) and an olefin co-feed with a supported cobalt-manganese Fischer-Tropsch synthesis catalyst to provide the product composition;

wherein the olefin co-feed comprises at least one $C_2$-$C_{14}$ olefin and is present in an amount in the range of 0.001 wt % to 40 wt % relative to the total amount of hydrogen, the gaseous carbon oxide and olefin;

wherein a weight ratio of manganese to cobalt in the catalyst is at least 0.05 on an elemental basis; and wherein the molar ratio of hydrogen to the gaseous carbon oxide in the mixture of hydrogen and the gaseous carbon oxide is at least 0.5.

Thus, the present disclosure provides a process for converting a mixture of hydrogen and gaseous carbon oxide to a composition comprising alcohols and liquid hydrocarbons by means of a Fischer-Tropsch synthesis reaction, said process comprising contacting a mixture of hydrogen and gaseous carbon oxide, preferably in the form of synthesis gas mixture, with a supported Co—Mn Fischer-Tropsch synthesis catalyst. The product composition produced by the Fischer-Tropsch synthesis reaction will also comprise other components, such as longer chain hydrocarbons (e.g., waxes) as well as other oxygenates. Critically, however, the processes of the disclosure can exhibit an increase in selectivity to alcohols as compared to conventional Fischer-Tropsch processes using a cobalt-based catalyst and even as compared to Fischer-Tropsch processes using cobalt-manganese catalysts described in International Patent Application Publication no. 2019/154885 and the Paterson et al. paper.

The term "liquid hydrocarbons" used herein in reference to the products of the Fischer-Tropsch reaction refers to $C_4$ to $C_{24}$ hydrocarbons. In certain embodiments as otherwise described herein, the liquid hydrocarbons are predominantly linear hydrocarbons, e.g., at least 50 wt %, at least 75 wt %, or even at least 90 wt % linear hydrocarbons.

The present inventors note that the use of a cobalt-manganese catalyst can provide a degree of olefinic character to the liquid hydrocarbons. In certain embodiments as otherwise described herein, the liquid hydrocarbons comprise at least 1 wt % olefins, for example at least 2 wt % olefins or at least 3 wt % olefins. In certain such embodiments, the liquid hydrocarbons include at least 5 wt % olefins, e.g., at least 10 wt % olefins, or at least 20 wt % olefins. In certain desirable embodiments, the olefins of the liquid hydrocarbons will comprise linear alpha olefins, e.g., at least 50 wt % linear alpha olefins, or even at least 70 wt % linear alpha olefins. But other products are possible. In certain embodiments, the olefins of the liquid hydrocarbons comprise cyclic olefins. In certain embodiments as otherwise described herein, the olefins of the liquid hydrocarbons comprise branched olefins, in which the branched olefins are terminal olefins that are internal to a chain (e.g., for olefins of formula $H_2C\!\!=\!\!C(R^A)(R^B)$, neither $R^A$ nor $R^B$ are H).

The term "alcohol" as used herein in reference to the products of the Fischer-Tropsch reaction refers to an alcohol having any number of carbon atoms. For example, in certain embodiments the alcohols of the Fischer-Tropsch product have from one to 30 carbons. The alcohols are typically acyclic and may be straight- or branched-chain, preferably straight-chain. In certain embodiments as otherwise described herein, the alcohols comprise at least 50 wt % linear alpha alcohols, such as at least 70 wt % linear alpha alcohols or at least 80 wt % linear alpha alcohols.

The processes described herein can provide alcohols of a variety of carbon numbers. In certain embodiments as otherwise described, the alcohols prepared by the process of the present disclosure include a major proportion (at least 50 wt %) of short- and medium-chain length $C_1$ to $C_8$ alcohols, for example, at least 75 wt % $C_1$ to $C_8$ alcohols or even at least 90 wt % $C_1$ to $C_8$ alcohols. But in other embodiments, the alcohols prepared by the process of the present disclosure include a major proportion (above 50 wt %) long-chain length $C_9$ to $C_{25}$ alcohols. In some embodiments, the alcohol composition can depend on the nature of the olefin co-feed as otherwise described herein. For example, it certain embodiments the alcohols contains an increased proportion of the carbonylation product of the olefin co-feed. For example, in an embodiment where the olefin co-feed comprises a $C_nH_{2n}$ olefin, the alcohol product composition comprises an increased proportion of the $C_{n+1}H_{2n+1}OH$ alcohol, (e.g., in the case of a propene co-feed, butanol). But the present inventors note that a variety of other alcohols are also produced. The amount of alcohols produced by the Fischer-Tropsch reaction, and their relative proportions are determined by GC mass spectrometry; in cases where conventional GC does not provide sufficient resolution, a two-dimensional GC×GC technique can be used, e.g., using different columns.

In certain embodiments as otherwise described herein, the process of the disclosure has a selectivity for alcohols (e.g., for $C_1$-$C_{24}$ alcohols, or for $C_1$-$C_8$ alcohols) of at least 10%, e.g., at least 15%. In certain embodiments as otherwise described herein, a process of the disclosure as otherwise described herein has a selectivity for alcohols (e.g., for $C_1$-$C_{24}$ alcohols, or for $C_1$-$C_8$ alcohols) of at least 20%, e.g., at least 25%. In certain such embodiments, the selectivity for alcohols (e.g., for $C_1$-$C_{24}$ alcohols, or for $C_1$-$C_8$ alcohols) is at least 40%, e.g. at least 50%, at least 60%, or greater than 70%. As used herein, "selectivity" for a given component is measured as the molar fraction of the gaseous carbon oxide that is reacted in the process (i.e., not including any unreacted portion of the gaseous carbon oxide) and is converted to that product. For example, in embodiments in which the gaseous carbon oxide is carbon monoxide, "selectivity" for a given component is defined as the molar fraction of carbon monoxide that is reacted in the process and is converted to the product of interest, not including any unreacted carbon monoxide.

Notably, the use of cobalt-manganese catalysts in Fischer-Tropsch syntheses as described herein can also provide longer chain alcohols. For example, in certain embodiments as otherwise described herein, at least 10 wt % (e.g., at least 15 wt %) of the products having 8 to 24 carbon atoms are alcohols. For example, in certain embodiments, at least 20 wt % (e.g., at least 25 wt %) of the products having 1 to 24 carbon atoms are alcohols. In certain such embodiments, no more than 90 wt %, e.g., no more than 80 wt %, of the products having 8 to 24 carbon atoms are alcohols.

While the measurement of $C_1$-$C_8$ alcohols is common within the art due to process limitations, in many cases $C_1$-$C_8$ alcohol production within a Fischer-Tropsch process is generally representative of overall alcohol production (e.g., $C_1$-$C_{24}$ alcohol production). Accordingly, experimental results with respect to $C_1$-$C_8$ alcohol production can often be extrapolated to provide an indication of overall $C_1$-$C_{24}$ alcohol production (see Examples).

Without wishing to be bound by theory, it is believed that preparing a catalyst that comprises at least 0.5 wt. % manganese and a manganese to cobalt weight ratio, on an elemental basis, of at least 0.05, by impregnation, the cobalt oxide crystallite sizes in the resulting supported Co—Mn Fischer-Tropsch synthesis catalyst are of a particle size which may give rise to, or contribute to, benefits when the catalyst is utilized in a Fischer-Tropsch reaction. In certain embodiments of the disclosure, the cobalt oxide crystallite (e.g., $Co_3O_4$) particle sizes resulting from the combination of total amount of manganese and the weight ratio manganese to cobalt weight ratio as described herein are less than 150 Angstroms (15 nm), for example less than 100 Angstroms (10 nm), preferably less than 80 Angstroms (8 nm). Once the Co—Mn Fischer-Tropsch synthesis catalyst is activated and utilized in a Fischer-Tropsch reaction, productivity and selectivity for alcohols can be notably enhanced over cobalt-containing synthesis catalysts comprising no manganese, or an insufficient amount of manganese. Additionally, without being bound by theory, it is believed that the productivity and selectivity for olefins is notably enhanced over cobalt-containing synthesis catalysts comprising no manganese, or an insufficient amount of manganese.

Without being bound by any particular theory, it is believed that the presence of manganese contributes to surface effects on the solid support that influence cobalt oxide crystallite development and dispersivity at the surface. This may derive from the mobility of cobalt-containing precursor compound(s) which are applied to the support material during catalyst preparation, for instance suspended or dissolved in an impregnation solution, whilst in the presence of manganese-containing precursor compound(s). Thus, catalysts especially suitable for use herein can involve cobalt-containing precursor compound(s) and manganese-containing precursor compound(s) being applied to a support material such that they form a mobile admixture at the surface of the support during its preparation.

As described above, inventors have found FT catalysts that comprise mixtures of cobalt and manganese as especially suitable for increasing alcohol production. In certain embodiments as otherwise described herein, the weight ratio of manganese to cobalt present in the synthesis catalyst is in the range of 0.05 to 3.0 on an elemental basis. For example, in particular embodiments, the weight ratio is in the range of 0.05 to 2.5, or 0.05 to 2.0, or 0.05 to 1.5, or 0.05 to 1.2, or 0.05 to 1, or 0.2 to 3.0, or 0.2 to 2.5, or 0.2 to 2.0, or 0.2 to 1.5, or 0.2 to 1.2, or 0.2 to 1, or 0.3 to 3.0, or 0.3 to 2.5, or 0.3 to 2.0, or 0.3 to 1.5, or 0.3 to 1.2, or 0.3 to 1, or 0.5 to 3.0, or 0.5 to 2.5, or 0.5 to 2.0, or 0.5 to 1.5, or 0.5 to 1.

Suitable synthesis catalysts typically may possess a wide variety of transition metal loadings. In certain embodiments as otherwise described herein, the synthesis catalyst comprises at least 0.5 wt % manganese on an elemental basis. In certain embodiments, the synthesis catalyst comprises up to 25 wt % manganese on an elemental basis. For example, the synthesis catalyst may comprise manganese in the range of 0.5 to 25 wt % on an elemental basis, for example, 0.5 to 25 wt %, or 0.5 to 20 wt %, or 0.5 to 15 wt %, or 0.5 to 12 wt %, or 1 to 12 wt %, or 1 to 12 wt %, or 1 to 12 wt %, or 1 to 11 wt %, or 1.5 to 11 wt %, or 1.5 to 10 wt %, or 2 to 10 wt %. Alternatively, the synthesis catalyst may comprise at least 2.5 wt % manganese on an elemental basis, for example, 3 to 25 wt %, or 4 to 20 wt %, or 5 to 15 wt %, or 2.5 to 12 wt %, or 3 to 12 wt %, or 4 to 12 wt %, or 5 to 12 wt %, or 2.5 to 11 wt %, or 3 to 11 wt %, or 4 to 11 wt %, or 5 to 11 wt %, or 2.5 to 10 wt %, or 3 to 10 wt %, or 4 to 10 wt %, or 5 to 10 wt %.

In certain embodiments as otherwise described herein, the synthesis catalyst comprises at least 0.5 wt % cobalt on an elemental basis. In certain embodiments, the synthesis catalyst comprises up to 35 wt % cobalt on an elemental basis. For example, in certain embodiments, the synthesis catalyst comprises cobalt in an amount of 0.5-35 wt %, for example, 0.5 to 25 wt %, or 0.5 to 20 wt %, or 0.5 to 15 wt %, or 0.5 to 12 wt %, or 1 to 12 wt %, or 1 to 12 wt %, or 1 to 12 wt %, or 1 to 11 wt %, or 1.5 to 11 wt %, or 1.5 to 10 wt %, or 2 to 10 wt %, or 5-35 wt %, or 7-35 wt %, or 10-35 wt %, or 2-25 wt %, or 5-25 wt %, or 7-25 wt %, or 10-25 wt %, on an elemental basis. In certain particular embodiments, the synthesis catalyst comprises cobalt in an amount of 2-20 wt %, e.g., 5-20 wt %, or 7-20 wt %, or 10-20 wt %, or 2-15 wt %, or 5-15 wt %, or 7-15 wt %, an elemental basis.

In certain embodiments as otherwise described herein, the total amount of cobalt and manganese in the synthesis catalyst is no more than 40 wt % on an elemental basis, based on the total weight of the synthesis catalyst. For example, in particular embodiments the total amount of cobalt and manganese in the synthesis catalyst is no more than 30 wt %, or no more than 25 wt %, or no more than 22 wt %, or no more than 20 wt %. In certain embodiments, the total amount of cobalt and manganese in the synthesis catalyst is no more than 15 wt %. In certain embodiments as otherwise described herein, the total amount of cobalt and manganese in the synthesis catalyst is at least 2 wt % on an elemental basis, based on the total weight of the synthesis catalyst. For example, in particular embodiments the total amount of cobalt and manganese in the synthesis catalyst is at least 5 wt %, or at least 8 wt %, or at least 10 wt %.

In yet a further aspect of the disclosure, there is provided a supported Co—Mn Fischer-Tropsch synthesis catalyst comprising cobalt oxide crystallites having a particle size of less than 150 Angstroms (15 nm), preferably less than 100 Angstroms (10 nm), or less than 80 Angstroms (8 nm), and comprising at least 0.5 wt % of manganese, on an elemental basis, based on the total weight of the supported synthesis catalyst; and wherein the weight ratio of manganese to cobalt, on an elemental basis, is 0.0.05 or greater, and the support material of the supported Co—Mn Fischer-Tropsch synthesis catalyst comprises a material selected from alumina, zirconia, zinc oxide, ceria, silica and titania. For example, in particular embodiments, the synthesis catalyst comprises a support material that comprises titania, or is titania.

In yet a further aspect of the disclosure, there is provided a supported Co—Mn Fischer Tropsch synthesis catalyst comprising at least 0.5 wt % of manganese, on an elemental basis, based on the total weight of the supported synthesis catalyst; and wherein the weight ratio of manganese to cobalt present, on an elemental basis, is 0.05 or greater, the support material of the supported Co—Mn Fischer-Tropsch synthesis catalyst comprises a material selected from titania, zinc oxide, zirconia, silica, alumina and ceria, and wherein the catalyst comprising cobalt oxide crystallites having a particle size of less than 150 Angstroms (15 nm), preferably less than 100 Angstroms (10 nm).

In certain processes as described herein, the Fischer-Tropsch synthesis reaction is conducted at a pressure in the range of from 10 to 100 bar (1.0 to 10.0 MPa) absolute. In preferred embodiments, the pressure of the Fischer-Tropsch reaction is in the range from 10 to 80 bar (from 1 to 8 MPa), e.g., from 10 to 60 bar (from 1 to 6 MPa), for example from 15 to 50 bar (from 1.5 to 5 MPa) or from 20 to 45 bar (from 2 to 4.5 MPa).

The supported Co—Mn Fischer-Tropsch synthesis catalyst used in accordance with the present disclosure may be prepared by any suitable method which is able to provide the required manganese to cobalt weight ratio and the required concentration of manganese on the supported. Preferably, the supported Co—Mn Fischer-Tropsch synthesis catalyst used in accordance with the present disclosure is prepared by a process in which the cobalt and the manganese are impregnated on to the support material.

A suitable impregnation method, for example, comprises impregnating a support material with cobalt-containing compound, which is thermally decomposable to the oxide form, and a manganese-containing compound. Impregnation of the support material with the cobalt-containing compound and the manganese-containing compound may be achieved by any suitable method of which the skilled person is aware, for instance by vacuum impregnation, incipient wetness or immersion in excess liquid.

The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation.

The support material may be in the form of a powder, granulate, shaped particle, such as a preformed sphere or microsphere, or extrudate. Reference herein to a powder or granulate of a support material is understood to refer to free flowing particles of a support material or particles of support material that have undergone granulation and/or sieving to be a particular shape (e.g. spherical) and size range. Reference herein to an "extrudate" is intended to mean a support material that has undergone an extrusion step and therefore may be shaped. In the context of the present disclosure, the powder or granulate is in a form which is suitable for impregnation with a solution of cobalt-containing compound and manganese-containing compound, and subsequent extrusion or forming into other shaped particles.

The support material serves to bind the catalyst particles and may also influence the catalytic activity. In certain embodiments as otherwise described herein, the support material comprises one or more oxide selected from the group consisting of alumina, zirconia, zinc oxide, ceria, silica and titania. In particular embodiments, the support material is one of alumina, zirconia, zinc oxide, ceria, silica and titania. For example, in certain embodiments, the catalyst comprises titania (e.g., the support material is titania).

It will be understood that the support material may be in any form provided it is suitable for use as a support for a Fischer-Tropsch synthesis catalyst and also preferably where the support material has not been previously impregnated with sources of metal (i.e., other than cobalt and/or manganese) that may have a deleterious effect on the performance of the active catalyst and may interfere with the benefits of the processes of the disclosure. Thus, whilst support material that has been previously loaded with cobalt and/or manganese metal, or precursors thereof, may be used in accordance with the disclosure, other pre-treatments providing sources of other metals are preferably to be avoided. Preferred support materials are substantially free of extraneous components which might adversely affect the catalytic activity of the system. Thus, preferred support materials are at least 95% w/w pure, more preferably at least 98% w/w pure and most preferably at least 99% w/w pure. Impurities preferably amount to less than 1% w/w, more preferably less than 0.50% w/w and most preferably less than 0.25% w/w. The pore volume of the support is preferably more than 0.150 ml/g and preferably more than 0.30 ml/g. The average pore radius (prior to impregnation) of the support material is 10 to 500 A, preferably 15 to 100 Angstroms, more preferably 20 to 80 A and most preferably 25 to 60 A. The BET surface area is suitably from 2 to 1000 $m^2g$, preferably from 10 to 600 $m^2/g$, more preferably from 15 to 300 $m^2/g$, and most preferably 30 to 150 $m^2/g$.

The BET surface area, pore volume, pore size distribution and average pore radius may be determined from the nitrogen adsorption isotherm determined at 77K using a Micromeritics TRISTAR 3000 static volumetric adsorption analyser. A procedure which may be used is an application of British Standard methods BS4359: Part 1:1984 'Recommendations for gas adsorption (BET) methods' and BS7591: Part 2:1992, 'Porosity and pore size distribution of materials'—Method of evaluation by gas adsorption. The resulting data may be reduced using the BET method (over the pressure range 0.05-0.20 P/Po) and the Barrett, Joyner & Halenda (BJH) method (for pore diameters of 20-1000 Angstroms) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, LG & Halenda P P, J. Am Chem. Soc., 1951 73 373-380.

When in the form of a powder, the median particle size diameter (d50) is preferably less than 50 μm, more preferably less than 25 μm. When the support material is in the form of a granulate, the median particle size diameter (d50) is preferably from 300 to 600 μm. Particle size diameter (d50) may suitably be determined by means of a particle size analyser (e.g. Microtrac S3500 Particle size analyser).

It is known to be beneficial to perform Fischer-Tropsch catalysis with a shaped particle, such as an extrudate, particularly in the case of fixed catalyst bed reactor systems. For instance, it is known that, for a given shape of catalyst particles, a reduction in the size of the catalyst particles in a fixed bed gives rise to a corresponding increase in pressure drop through the bed. Thus, the relatively large shaped particles cause less of a pressure drop through the catalyst bed in the reactor compared to the corresponding powdered or granulated supported catalyst. Shaped particles, such as extrudates, also generally have greater strength and experience less attrition, which is of particular value in fixed bed arrangements where bulk crush strength must be very high.

Reference herein to "impregnation" or "impregnating" is intended to refer to contact of the support material with a solution, or solutions, of, for example, a cobalt-containing compound and a manganese-containing compound, before drying in order to achieve precipitation of the cobalt-containing compound and the manganese-containing compound. Impregnation with a fully dissolved solution, or solutions, of a cobalt-containing compound and a manganese-containing compound ensures good dispersion of the cobalt-containing compound and the manganese-containing compound on the support material and is thus preferred. This is in contrast, for instance, to the use of partially dissolved cobalt-containing compound and/or a partially dissolved manganese-containing compound in 'solid solutions' or suspensions, where the level of dispersion of the cobalt-containing compound and manganese-containing compound across the surface, and in the pores, of the support material can fluctuate depending on the nature of the precipitation on the support material. Furthermore, use of a fully dissolved solution, or solutions, of cobalt-containing compound and manganese-containing compound also has less of an impact upon the resulting morphology and bulk crush strength of an extrudate formed thereafter compared with solid solutions. Nevertheless, benefits of the processes of the present disclosure can also be realised in the case where a solid solution, or solutions, of a partially undissolved cobalt-containing compound and/or manganese-containing compound is used.

Where a powder or granulate of a support material is contacted with a solution, or solutions, of cobalt-containing compound and manganese-containing compound, the amount of solution used preferably corresponds to an amount of liquid which is suitable for achieving a mixture which is of a suitable consistency for further processing, for example for shaping by extrusion. In that case, complete removal of the solvent of the impregnating solution may be effected after formation of the shaped particle, such as an extrudate.

Suitable cobalt-containing compounds are those which are thermally decomposable to an oxide of cobalt following calcination and which are preferably completely soluble in the impregnating solution. Preferred cobalt-containing compounds are the nitrate, acetate or acetylacetonate of cobalt, most preferably the nitrate of cobalt, for example cobalt nitrate hexahydrate. It is preferred to avoid the use of the halides because these have been found to be detrimental.

Suitable manganese-containing compounds are those which are thermally decomposable following calcination and which are preferably completely soluble in the impregnating solution. Preferred manganese-containing compounds are the nitrate, acetate or acetylacetonate of manganese, most preferably the acetate of manganese.

The solvent of the impregnating solution(s) may be either an aqueous solvent or a non-aqueous, organic solvent. Suitable non-aqueous organic solvents include, for example, alcohols (e.g. methanol, ethanol and/or propanol), ketones (e.g. acetone), liquid paraffinic hydrocarbons and ethers. Alternatively, aqueous organic solvents, for example an aqueous alcoholic solvent, may be employed. Preferably, the solvent of the impregnating solution(s) is an aqueous solvent.

In preferred embodiments, the impregnation of the support material with a cobalt-containing compound and a manganese-containing compound occurs in a single step, without any intermediate drying or calcination steps to separate the loading of the different components. As the skilled person will appreciate, the cobalt-containing compound and manganese-containing compound may be applied to the support material successively or simultaneously in separate impregnation solutions or suspensions, or preferably an impregnation solution or suspension comprising both the cobalt-containing compound and the manganese-containing compound is used.

The concentration of the cobalt-containing compound and the manganese-containing compound, in the impregnating solution(s) is not particularly limited, although preferably the cobalt-containing compound and the manganese-containing compound are fully dissolved, as discussed hereinbefore. When a powder or granulate of support material is impregnated and immediately followed by an extrusion step, the amount of the impregnating solution(s) is preferably suitable for forming an extrudable paste.

In a preferred embodiment, the concentration of the impregnating solution is sufficient to afford a supported catalyst containing from 5 wt % to 35 wt % of cobalt, more preferably from 7.5 wt % to 25 wt % of cobalt, even more preferably from 10 to 20 wt % of cobalt, on an elemental basis, based on the total weight of the supported synthesis catalyst.

In another preferred embodiment, the concentration of the impregnating solution is sufficient to afford a supported catalyst containing from 0.5 wt % to 15 wt % of manganese, preferably from 3.0 wt % to 10.5 wt % of manganese, for example from 3.0 to 10 wt % of manganese, or even 4.0 to 8.0 wt % of manganese, on an elemental basis, based on the total weight of the supported synthesis catalyst, following drying and calcination.

A suitable concentration of cobalt-containing compound and/or manganese-containing compound is, for example, 0.1 to 15 moles/litre.

It will be appreciated that where the support material is in powder or granulate form, once impregnated with a cobalt containing compound and a manganese-containing compound, the impregnated support material may be extruded or formed into shaped particles at any suitable stage before or after drying and calcining.

Impregnation of the support material is usually followed by drying of the impregnating solution in order to effect precipitation of the cobalt-containing compound and the manganese-containing compound on to the support material and preferably also to remove bound solvent of the impregnating solution (e.g. water). Drying therefore does not, for instance, lead to full decomposition of the cobalt-containing compound or otherwise lead to a change in oxidation state of the cobalt-containing compound. As will be appreciated, in embodiments where an extrusion is performed, complete drying and removal of solvent (e.g. bound solvent) of the impregnating solution may occur after forming of a shaped particle, for example by extrusion. Drying is suitably conducted at temperatures from 50° C. to 150° C., preferably 75° C. to 125° C. Suitable drying times are, for example, from 5 minutes to 72 hours. Drying may suitably be conducted in a drying oven or in a box furnace, for example, under the flow of an inert gas at elevated temperature.

Where a shaped particle, such as an extrudate, is impregnated, it will be appreciated that the support may be contacted with the impregnating solution by any suitable means including, for instance, vacuum impregnation, incipient wetness or immersion in excess liquid, as mentioned hereinbefore. Where a powder or granulate of support material is impregnated, the powder or granulate may be admixed with the impregnating solution by any suitable means of which the skilled person is aware, such as by adding the powder or granulate to a container of the impregnating solution and stirring.

Where a step of forming a shaped particle, such as an extrusion step, immediately follows impregnation of a powder or granulate, the mixture of powder or granulate and impregnating solution may be further processed if it is not already in a form which is suitable for forming a shaped particle, for instance by extrusion. For instance, the mixture may be mulled to reduce the presence of larger particles that may not be readily extruded or otherwise formed into a shaped particle, or the presence of which would otherwise compromise the physical properties of the resulting shaped particle, for example an extrudate. Mulling typically involves forming a paste which is suitable for shaping, such as by extrusion. Any suitable mulling or kneading apparatus of which the skilled person is aware may be used for mulling in the context of the present disclosure. For example, a pestle and mortar may suitably be used in some applications or a Simpson muller may suitably be employed. Mulling is typically undertaken for a period of from 3 to 90 minutes, preferably for a period of 5 minutes to 30 minutes. Mulling may suitably be undertaken over a range of temperatures, including ambient temperatures. A preferred temperature range for mulling is from 15° C. to 50° C. Mulling may suitably be undertaken at ambient pressures. As stated hereinbefore, it will be appreciated that complete removal of bound solvent from the impregnation solution may be conducted to effect complete precipitation after forming of the shaped particle, such as by extrusion.

In embodiments where a calcination step is performed on an impregnated powder or granulate, thereby completely removing solvent of the impregnation solution, the calcined powder or granulate may also be further processed in order to form a mixture which is suitable for forming into shaped particles, for example by extruding. For instance, an extrudable paste may be formed by combining the calcined powder or granulate with a suitable solvent, for example a solvent used for impregnation, preferably an aqueous solvent, and mulled as described above.

Preparation of the supported Co—Mn Fischer-Tropsch synthesis catalyst involves a calcination step. As will be understood, calcination is required for converting the cobalt-containing compound which has been impregnated on the support material into an oxide of cobalt. Thus, calcination leads to thermal decomposition of the cobalt-containing compound, and not merely removal of bound solvent of an impregnating solution, as for instance in the case of drying.

Calcination may be performed by any method known to those of skill in the art, for instance in a fluidized bed or rotary kiln at a temperature of at least 250° C., preferably from 275° C. to 500° C. In some embodiments, calcination may be conducted as part of an integrated process where calcination and reductive activation of the synthesis catalyst to yield a reduced Fisher-Tropsch synthesis catalyst are performed in the same reactor. In a particularly preferred embodiment, the supported Co—Mn Fischer-Tropsch synthesis catalyst used in the process of the disclosure is obtained or obtainable from a process comprising the steps of:

(a) impregnating a support material with: a cobalt-containing compound and a manganese-containing compound in a single impregnation step to form an impregnated support material; and (b) drying and calcining the impregnated support material to form the supported Co—Mn Fischer-Tropsch synthesis catalyst.

A particular advantage of this embodiment is the expediency with which a support material may be modified and converted into a supported Co—Mn Fischer-Tropsch synthesis catalyst using only a single impregnation step followed by a drying and calcination step. Thus, in preferred embodiments, the support material used in connection with the processes of the disclosure has undergone no prior modification, for instance by the addition of promoters, dispersion aids, strength aids and/or binders, or precursors thereof, before impregnation in step (a) of the process.

The supported Co—Mn Fischer-Tropsch synthesis catalyst used in the process of the present disclosure may additionally comprise one or more promoters, dispersion aids or binders. Promoters may be added to promote reduction of an oxide of cobalt to cobalt metal, preferably at lower temperatures. Preferably, the one or more promoters is selected from the list consisting of ruthenium, palladium, platinum, rhodium, rhenium, chromium, nickel, iron, molybdenum, tungsten, zirconium, gallium, thorium, lanthanum, cerium, copper and mixtures thereof. Promoter is typically used in a cobalt to promoter atomic ratio of up to 250:1 and more preferably up to 125:1, still more preferably up to 25:1, and most preferably 10:1. In preferred embodiments, the one or more promoters are present in the cobalt-containing Fischer-Tropsch synthesis catalyst obtained in an amount from 0.1 wt % to 3 wt %, on an elemental basis, based on the total weight of the supported synthesis catalyst. In other preferred embodiments, the cobalt-containing Fischer-Tropsch synthesis catalyst does not comprise any promoters.

The addition of the promoters, dispersion aids, strength aids, or binders may be integrated at several stages of the catalyst preparation process. Preferably, the promoters, dispersion aids or binders, or precursors thereof, is/are introduced during impregnation step(s) where the cobalt-containing compound and manganese-containing compound are introduced. The supported Co—Mn Fischer-Tropsch synthesis catalyst may conveniently be converted into a reduced supported Co—Mn Fischer-Tropsch synthesis catalyst by reductive activation by any known means of which the skilled person is aware which is capable of converting cobalt oxide to the active cobalt metal. Thus, in one embodiment, the process of the disclosure further comprises a preceding step of reducing a Co—Mn Fischer-Tropsch synthesis catalyst to form a reduced Co—Mn Fischer-Tropsch synthesis catalyst by contacting with a hydrogen-containing gas stream. The step of forming a reduced synthesis catalyst may be carried out batch wise or continuously in a fixed bed, fluidised bed or slurry phase reactor, or in-situ in the same reactor as will be subsequently used for the Fischer-Tropsch synthesis reaction. Reduction is suitably performed at a temperature of from 150° C. to 500° C., preferably from 200° C. to 400° C., more preferably from 250° C. to 350° c.

As will be appreciated, the gaseous reactant mixture supplied to the Fischer-Tropsch reaction may also be suitable for reducing the supported Co—Mn Fischer-Tropsch synthesis catalyst to form a reduced supported Co—Mn Fischer-Tropsch synthesis catalyst in situ, without requiring any preceding or distinct reductive activation step.

In the Fischer-Tropsch reaction of the disclosure, the volume ratio of hydrogen to the gaseous carbon oxide ($H_2$:$CO_x$) in the gaseous reactant mixture is at least 0.5:1, preferably at least 1:1, more preferably at least 1.2:1, more preferably at least 1.3:1, more preferably at least 1.4:1, more preferably at least 1.5:1, or even at least 1.6:1. In some or all embodiments of the present disclosure, the volume ratio of hydrogen to the gaseous carbon oxide ($H_2$:$CO_x$) in the gaseous reactant mixture is at most 5:1, preferably at most 3:1, most preferably at most 2.2:1. Examples of suitable volume ratios of hydrogen to the gaseous carbon oxide ($H_2$:$CO_x$) in the gaseous reactant mixture include the ranges: from 1:1 to 5:1; from 1.1:1 to 3:1; from 1.2:1 to 3:1; from 1.3:1 to 2.2:1; from 1.4:1 to 5:1; from 1.4:1 to 3:1; from 1.4:1 to 2.2:1; from 1.5:1 to 3:1; from 1.5:1 to 2.2:1; and, from 1.6:1 to 2.2:1. The gaseous reactant stream may also comprise other gaseous components, such as nitrogen, water, methane and other saturated and/or unsaturated light hydrocarbons, each preferably being present at a concentration of less than 30% by volume.

As discussed hereinbefore, the Fischer-Tropsch synthesis process of the present disclosure has been surprisingly found to afford a Fischer-Tropsch catalyst exhibiting high selectivity for alcohols; the Fischer-Tropsch synthesis process of the present disclosure has also been surprisingly found to afford a Fischer-Tropsch catalyst exhibiting high selectivity for olefins. Furthermore, at least in some embodiments, the catalytic activity has also been found to be superior.

Conventional Fischer-Tropsch temperatures may be used in order to prepare alcohols and liquid hydrocarbons in accordance with the present disclosure. For example, the temperature of the contacting of a mixture of hydrogen and the gaseous carbon oxide (e.g., in the form of a synthesis gas mixture) and an olefin co-feed with a supported cobalt-manganese Fischer-Tropsch catalyst may suitable be in the range from 100 to 400° C., such as from 100 to 350° C., or 100 to 300° C., or 100 to 250° C., or 150 to 400° C., or 150 to 350° C., or 150 to 300° C., or 150 to 250° C. In certain embodiments, the contacting is conducted at a temperature of no more than 350° C., e.g., no more than 325° C., or no more than 300° C., or no more than 280° C., or no more than 260° C. The pressure of the contacting (i.e., the temperature of the Fischer-Tropsch reaction) can in certain embodiments suitably be in the range from 10 to 100 bara (from 1 to 10 MPa), such as from 15 to 75 bara (from 1.5 to 7.5 MPa), or from 20 to 50 bara (from 2.0 to 5.0 MPa). For example, in certain embodiments the contacting is conducted at a pressure of no more than 7.5 MPa absolute.

In particular embodiments, the temperature of the Fischer-Tropsch reaction is in the range from 150 to 350° C., more preferably from 180 to 300° C., and most preferably from 200 to 260° C. In preferred embodiments, the pressure of the Fischer-Tropsch reaction is in the range from 10 to 100 bar (from 1 to 10 MPa), more preferably from 10 to 60 bar (from 1 to 6 MPa) and most preferably from 20 to 45 bar (from 2 to 4.5 MPa).

The present disclosure provides for the reaction between a mixture of hydrogen gas and a gaseous carbon oxide. In certain embodiments as otherwise described herein, the gaseous carbon oxide is carbon monoxide. The carbon monoxide can be provided, e.g., with substantially no carbon dioxide. However, in other embodiments, the gaseous carbon oxide is carbon dioxide or a carbon monoxide in combination with carbon dioxide.

The present inventors have surprisingly found that the addition of an olefin co-feed into the Fischer-Tropsch reaction mixture can advantageously improve the process selectivity for alcohols. Beyond direct and efficient conversion of the olefin feed, which would be a beneficial result alone, the increase in recovered alcohol content can be in excess of the amount expected based on the amount expected from the olefin feed alone, even controlling for the increase in molecular weight of the alcohol product relative to the olefin reactant. This unexpected result allows for the selective synthesis of alcohols in high yield through the tuning of the olefin co-feed composition and feed rate.

Without wishing to be bound by theory, it is presently believed that at least one product of an olefin co-feed comprising a $C_n$ olefin (i.e., an unsaturated hydrocarbon with n carbons) is reaction with the gaseous carbon oxide (e.g., carbon monoxide) and optionally hydrogen to form a $C_{n+1}$ alcohol. For example, a co-feed comprising propene may give rise to a product stream containing butanol. Under this theory, the skilled person may advantageously selected a particular olefin co-feed in order to produce a product stream with an increased amount of a desired alcohol product.

The olefin co-feed may be present in a wide variety of proportions by weight to achieve this result. In certain embodiments as otherwise described herein, the olefin co-feed is present in an amount in the range of 0.001 wt % to 30 wt %, e.g., 0.001 wt % to 20 wt %, or 0.001 wt % to 10 wt %, or 0.001 wt % to 15 wt %, or 0.001 wt % to 5 wt % relative to the total amount of hydrogen, gaseous carbon oxide and olefin. For example, in certain embodiments, the olefin co-feed is present in an amount in the range of 0.01 wt % to 30 wt %, e.g., 0.01 wt % to 15 wt %, 0.01 wt % to 10 wt %, or 0.01 wt % to 5 wt %, relative to the total amount of hydrogen, gaseous carbon oxide and olefin. In further embodiments, the olefin co-feed is present in an amount in the range of 0.1 wt % to 20 wt %, e.g., 0.1 wt % to 15 wt %, 0.1 wt % to 10 wt %, or 0.1 wt % to 5 wt %, relative to the total amount of hydrogen, gaseous carbon oxide and olefin. In further embodiments, the olefin co-feed is present in an amount in the range of 0.2 wt % to 20 wt %, e.g., 0.2 wt % to 15 wt %, 0.2 wt % to 10 wt %, or 0.2 wt % to 5 wt %, relative to the total amount of hydrogen, gaseous carbon oxide and olefin.

The olefin co-feed may have a variety of compositions based on feedstream availability and desired product composition. In certain embodiments as otherwise described herein, the olefin co-feed is at least 70 wt %, or at least 80 wt %, or at least 90 wt % $C_2$-$C_{14}$ olefins, or $C_2$-$C_{10}$ olefins. For example, in certain embodiments, the olefin co-feed is at least 70 wt %, or at least 80 wt %, or at least 90 wt % $C_2$-$C_5$ olefins. In particular embodiments, the olefin co-feed is at least 70 wt %, or at least 80 wt %, or at least 90 wt % propylene and/or ethylene. For example, the olefin co-feed may be over 95 wt % propylene. The olefins maybe a pure stream or comprise a mixture of olefins in a desired carbon range.

Olefins of various chemical structures may be utilized in order to tune the reaction conditions to achieve increased yields of particular products. Accordingly, in certain embodiments as otherwise described herein, the olefin co-feed comprises linear olefins (e.g., at least one linear olefin).

Examples of linear olefins include linear alpha-olefins (e.g., ethylene, propylene, 1-hexene, 1-heptene, 1-octene, and/or other suitable $C_2$-$C_{14}$ olefins) or internal linear olefins (e.g., 3-hexene and other suitable $C_2$-$C_{14}$ olefins). In certain embodiments as otherwise described herein, the olefin co-feed comprises cyclic olefins (e.g., at least one cyclic olefin). Examples of suitable cyclic olefins include cyclohexene, cycloheptene, cycloctene, bicyclic alkenes, and other suitable cyclic $C_4$-$C_{14}$ olefins). In certain embodiments as otherwise described herein, the olefin co-feed comprises branched olefins (e.g., at least one branched olefin). In particular embodiments, the at least one branched olefin is a terminal olefin (e.g., an alpha-olefin), wherein the olefin is internal. For example, in certain embodiments as otherwise described herein, the at least one branched olefin has a structure $(R^1)(R^2)C=CH_2$, wherein $R^1$ and $R^2$ are optionally substituted alkyl groups (i.e., neither $R^1$ nor $R^2$ are H). $R^1$ and $R^2$ may be linear or branched alkanes. They may be substituted with one or more group selected from hydroxy, halo, and amino.

The Fischer-Tropsch synthesis reaction may be performed in any suitable type of reactor, for example it may be performed in a fixed bed reactor, a slurry bed reactor, or a CANs reactor.

In another aspect of the disclosure, there is provided a supported Co—Mn Fischer-Tropsch synthesis catalyst comprising at least 0.5 wt % of manganese, on an elemental basis, based on the total weight of the supported synthesis catalyst; and wherein the weight ratio of manganese to cobalt present, on an elemental basis, is 0.05 or greater, the support material of the supported Co—Mn Fischer-Tropsch synthesis catalyst comprises a material selected from titania, zinc oxide, zirconia, silica and ceria, and wherein the supported Co—Mn Fischer-Tropsch synthesis is prepared by impregnation.

For the purposes of this disclosure, $Co_3O_4$ crystallite particle sizes are determined by X-ray diffraction.

As will be appreciated, the support material and methods for preparing the supported Co—Mn Fischer-Tropsch synthesis catalysts of the above further aspects of the disclosure may be as defined hereinbefore. For example, the synthesis catalysts are preferably obtained or obtainable from a process comprising the steps of:

(a) impregnating a support material with: a cobalt-containing compound and a manganese-containing compound in a single impregnation step to form an impregnated support material; and (b) drying and calcining the impregnated support material to form the supported Co—Mn Fischer-Tropsch synthesis catalyst.

The supported Co—Mn Fischer-Tropsch synthesis catalysts of the above further aspects of the disclosure may also be used for i) increasing the selectivity of a Fischer-Tropsch process for the production of alcohols; and/or ii) increasing conversion in a Fischer-Tropsch process.

In a yet further aspect of the disclosure, there is provided a method for controlling cobalt oxide crystallite size in the preparation of a supported cobalt-containing Fischer-Tropsch synthesis catalyst, said method comprising the step of supplying acetic acid, or a metal salt of acetic acid, during the impregnation of a support material with a cobalt-containing compound, wherein the metal is selected from the group consisting of ruthenium, palladium, platinum, rhodium, rhenium, manganese, chromium, nickel, iron, molybdenum, tungsten, zirconium, gallium, thorium, lanthanum, cerium, copper and mixtures thereof; preferably wherein the metal is selected from manganese, ruthenium, rhenium and platinum, more preferably the metal is manganese.

The processes of the disclosure will now be further described by reference to the following Examples which are illustrative only. In the Examples, CO conversion is defined as moles of CO used/moles of CO fed×100 and carbon selectivity as moles of CO attributed to a particular product/moles of CO converted×100. Unless otherwise stated, temperatures referred to in the Examples are applied temperatures and not catalyst/bed temperatures. Unless otherwise stated, pressures referred to in the Examples are absolute pressures.

EXAMPLES

The Examples that follow are illustrative of specific embodiments of the methods of the disclosure, and various uses thereof. They are set forth for explanatory purposes only, and are not to be taken as limiting the scope of the disclosure.

Example 1: Addition of Propene Co-Feed

Several Fischer-Tropsch catalysts of varying composition (see Table 1) were prepared by heating from 25° C. to 150° C. at 2° C./min, and then heating at 1° C./min from 150° C. to 300° C. in a 16 channel reactor with common feed, temperature and pressure between catalyst channels, with online analysis for $C_1$-$C_8$. The catalysts were activated at 300° C. under a 100% $H_2$ at atmospheric pressure and a 8000 $hr^{-1}$ gas hourly space velocity. A Fischer-Tropsch reaction was performed through contacting the respective catalyst with a 1.8 $H_2$:CO mixture with 20% $N_2$ gas at 30 barg and a 3000 $hr^{-1}$ gas hourly space velocity. To test the effect of olefin co-feed, olefin was introduced in place of the nitrogen gas co-feed.

The reactions were performed without an olefin co-feed (See "Baseline", below) and also with a 0.5 wt % propene co-feed. The results are summarized in Table 1, below:

optimization. The observed increases appear to be heavily dependent on the catalyst support material. This observation reinforces the theory that the addition of the olefin co-feed enhances the Fischer-Tropsch reaction dynamics beyond merely increasing the availability of unsaturated reactants. Importantly, the observed increase in alcohol selectivity is accomplished without detriment to $CH_4$ selectivity or $C_{5+}$ selectivity, both of which are not significantly changed by the addition of a propene co-feed.

It may be proposed that at least some of the increase in alcohol selectivity exhibited in Table 1 is a result of olefin transformation to the corresponding alcohol. While this is likely true, a 0.5 wt % propene feed, if fully converted to butanol, would be expected to produce approximately 0.9 wt % butanol, much less than the lowest observed increase in alcohol selectivity of +2.4 wt % observed in Table 1, and far below the average increase of +4.2 wt %. Accordingly, it is proposed that the olefin co-feed has an unexpected synergistic effect with the Fischer-Tropsch reaction, advantageously leading to increased alcohol production.

Various exemplary embodiments of the disclosure include, but are not limited to the enumerated embodiments listed below, which can be combined in any number and in any combination that is not technically or logically inconsistent.

Embodiment 1. A process for converting a mixture of hydrogen gas and a gaseous carbon oxide that is carbon monoxide, carbon dioxide, or a combination thereof to a product composition comprising alcohols and liquid hydrocarbons via a Fischer-Tropsch synthesis reaction, the process comprising:

contacting a mixture of hydrogen gas and the gaseous carbon oxide (e.g., in the form of a synthesis gas mixture) and an olefin co-feed with a supported cobalt-manganese Fischer-Tropsch synthesis catalyst to provide the product composition;

wherein the olefin co-feed comprises at least one $C_2$-$C_{14}$ olefin and is present in an amount in the range of 0.001

TABLE 1

| Catalyst Transition Metal | Support | Condition | CO Conversion % | $CH_4$ selectivity % | $C_{5+}$ Selectivity % | $C_1$-$C_8$ Alcohol Selectivity % | Change in Alcohol Selectivity % |
|---|---|---|---|---|---|---|---|
| 5% Mn/ 10% Co | $ZrO_2$ | Baseline | 22.2 | 5.7 | 69.8 | 26.3 | +6.0 |
| | | Propene Co-Feed | 23.2 | 6.0 | 68.3 | 32.3 | |
| 5% Mn/ 10% Co | ZnO | Baseline | 23.5 | 10.9 | 59.3 | 17.2 | +4.6 |
| | | Propene Co-Feed | 23.3 | 10.5 | 59.0 | 21.8 | |
| 5% Mn/ 10% Co | $CeO_2$ | Baseline | 20.9 | 8.7 | 64.5 | 28.3 | +4.6 |
| | | Propene Co-Feed | 21.2 | 8.8 | 64.2 | 32.9 | |
| 10% Mn/ 10% Co | $Al_2O_3$ | Baseline | 21.6 | 15.5 | 51.1 | 21.6 | +2.4 |
| | | Propene Co-Feed | 17.8 | 16.8 | 52.0 | 24.0 | |
| 10% Mn/ 10% Co | $TiO_2$ | Baseline | 22.3 | 4.4 | 73.6 | 13.8 | +3.2 |
| | | Propene Co-Feed | 25.0 | 4.4 | 73.2 | 17.0 | |

As can be seen in Table 1, the addition of an olefin co-feed such as a propene co-feed resulted in an increase in $C_1$-$C_8$ alcohol selectivity of an average of +4.2%. As known in the art, $C_1$-$C_8$ alcohol selectivity is typically representative of overall alcohol selectivity. Accordingly, it can be expected that the olefin co-feed increased the overall alcohol selectivity as well. Further increases are likely given further wt % to 40 wt % relative to the total amount of hydrogen, the gaseous carbon oxide and olefin;

wherein a weight ratio of manganese to cobalt in the catalyst is at least 0.05 on an elemental basis; and wherein the molar ratio of hydrogen to the gaseous carbon oxide in the mixture of hydrogen and the gaseous carbon oxide is at least 0.5.

2. The process of embodiment 1, wherein the weight ratio of manganese to cobalt present in the synthesis catalyst is in the range of 0.05 to 3.0 on an elemental basis (e.g., present in the range of 0.1 to 2.5, or 1.5 to 2.0, or 0.2 to 1.5, or 0.2 to 1.2, or 0.2 to 1, or 0.3 to 3.0, or 0.3 to 2.5, or 0.3 to 2.0, or 0.3 to 1.5, or 0.3 to 1.2, or 0.5 to 3.0, or 0.5 to 2.5, or 0.5 to 2.0, or 0.5 to 1.5, or 0.5 to 1).

3. The process of embodiment 1 or embodiment 2, wherein the synthesis catalyst comprises at least 0.5 wt % manganese on an elemental basis.

4. The process of embodiment 1 or embodiment 2, wherein the synthesis catalyst comprises up to 25 wt %, e.g., in the range of 2.5-25 wt % manganese on an elemental basis.

5. The process of any of embodiments 1-4, wherein the synthesis catalyst comprises cobalt in an amount of 2-35 wt %, e.g., 5-35 wt %, or 7-35 wt %, or 10-35 wt %, or 2-25 wt %, or 5-25 wt %, or 7-25 wt %, or 10-25 wt %, on an elemental basis.

6. The process of any of embodiments 1-4, wherein the synthesis catalyst comprises cobalt in an amount of 2-20 wt %, e.g., 5-20 wt %, or 7-20 wt %, or 10-20 wt %, or 2-15 wt %, or 5-15 wt %, or 7-15 wt %, an elemental basis.

7. The process of any of embodiments 1-6, wherein the total amount of cobalt and manganese in the synthesis catalyst is no more than 40 wt % on an elemental basis, based on the total weight of the synthesis catalyst.

8. The process of any of embodiments 1-7, wherein the synthesis catalyst comprises $Co_3O_4$ crystallites having a particle size of less than 150 Angstroms.

9. The process of any of embodiments 1-8, wherein the catalyst comprises a support material that comprises at least one oxide selected from alumina, zirconia, zinc oxide, ceria, silica and titania.

10. The process of any of embodiments 1-8, wherein the support material comprises titania (e.g., is titania).

11. The process of any of embodiments 1-10, wherein the contacting is conducted at a pressure in the range of 1.0 to 10.0 MPa absolute.

12. The process of any of embodiments 1-11, wherein the contacting is conducted at a pressure of no more than 7.5 MPa absolute.

13. The process of any of embodiments 1-12, wherein the contacting is conducted at a temperature of no more than 350° C.

14. The process of any of embodiments 1-13, wherein the gaseous carbon oxide is carbon monoxide.

15. The process of embodiment 14, wherein the gaseous carbon oxide is carbon dioxide or a mixture of carbon monoxide and carbon dioxide.

16. The process of any of embodiments 1-15, wherein the olefin co-feed is present in an amount in the range of 0.001 wt % to 30 wt %, e.g., 0.001 wt % to 10 wt %, or 0.001 wt % to 5 wt %, relative to the total amount of hydrogen, the gaseous carbon oxide and olefin.

17. The process of any of embodiments 1-15, wherein the olefin co-feed is present in an amount in the range of 0.1 wt % to 20 wt %, e.g., 0.1 wt % to 15 wt %, 0.1 wt % to 10 wt %, or 0.1 wt % to 5 wt %, relative to the total amount of hydrogen, the gaseous carbon oxide and olefin.

18. The process of any of embodiments 1-15, wherein the olefin co-feed is present in an amount in the range of 1 wt % to 20 wt %, e.g., 1 wt % to 15 wt %, 1 wt % to 10 wt %, or 1 wt % to 5 wt %, relative to the total amount of hydrogen, the gaseous carbon oxide and olefin.

19. The process of any of embodiments 1-18, wherein the olefin co-feed comprises at least one linear olefin.

20. The process of any of embodiments 1-19, wherein the olefin co-feed comprises at least one cyclic olefin.

21. The process of any of embodiments 1-20, wherein the olefin co-feed comprises at least one branched olefin.

22. The process of any embodiment 21, wherein the at least one branched olefin is a terminal olefin (e.g., an alpha olefin), wherein the olefin is internal.

23. The process of embodiment 21 or embodiment 22, wherein the branched olefin has a structure $(R^1)(R^2)$ $C{=}CH_2$, wherein $R^1$ and $R^2$ are optionally substituted alkyl groups.

24. The process of any of embodiments 1-23, wherein the olefin co-feed is at least 90% $C_2$-$C_{14}$ olefins.

25. The process of any of embodiments 1-23, wherein the olefin co-feed is at least 90% $C_2$-$C_{10}$ olefins.

26. The process of any of embodiments 1-23, wherein the olefin co-feed in at least 90% $C_2$-$C_5$ olefins.

27. The process of any of embodiments 1-23, wherein the olefin co-feed is at least 90% propylene and/or ethylene.

28. The process of any of embodiments 1-27, wherein the product composition comprises at least 10 wt % alcohols, e.g., at least 15 wt % alcohols.

29. The process of any of embodiments 1-28, wherein the product composition comprises at least 20 wt % alcohols, e.g., at least 25 wt % alcohols.

30. The process of any of embodiments 1-29, wherein the alcohols comprise $C_1$-$C_{24}$ alcohols.

31. The process of any of embodiments 1-30, wherein the alcohols comprise $C_1$-$C_8$ alcohols.

The particulars shown herein are by way of example and for purposes of illustrative discussion of certain embodiments of the present disclosure only and are presented in the cause of providing what is believed to be the most useful and readily understood description of the principles and conceptual aspects of various embodiments of the disclosure. In this regard, no attempt is made to show details associated with the methods of the disclosure in more detail than is necessary for the fundamental understanding of the methods described herein, the description taken with the examples making apparent to those skilled in the art how the several forms of the methods of the disclosure may be embodied in practice. Thus, before the disclosed processes and devices are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the methods of the disclosure (especially in the context of the following embodiments and claims) are to be construed to cover both the singular and the plural, unless otherwise indicated herein or clearly contradicted by context.

All methods described herein can be performed in any suitable order of steps unless otherwise indicated herein or otherwise clearly contradicted by context. The use of any and all examples, or exemplary language (e.g., "such as") provided herein is intended merely to better illuminate the methods of the disclosure and does not pose a limitation on the scope of the disclosure. No language in the specification should be construed as indicating any non-claimed element essential to the practice of the methods of the disclosure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

All percentages, ratios and proportions herein are by weight, unless otherwise specified.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the disclosure are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of various aspects of the disclosure are described herein, including the best mode known to the inventors for carrying out the methods described herein. Of course, variations on these described embodiments will become apparent to those of ordinary skill in the art upon reading the foregoing description. The skilled artisan will employ such variations as appropriate, and as such the methods of the disclosure can be practiced otherwise than specifically described herein. Accordingly, the scope of the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The phrase "at least a portion" as used herein is used to signify that, at least, a fractional amount is required, up to the entire possible amount.

In closing, it is to be understood that the various embodiments herein are illustrative of the methods of the disclosures. Other modifications that may be employed are within the scope of the disclosure. Thus, by way of example, but not of limitation, alternative configurations of the methods may be utilized in accordance with the teachings herein. Accordingly, the methods of the present disclosure are not limited to that precisely as shown and described.

What is claimed is:

1. A process for converting a mixture of hydrogen gas and a gaseous carbon oxide that is carbon monoxide, carbon dioxide, or a combination thereof to a product composition comprising alcohols and liquid hydrocarbons via a Fischer-Tropsch synthesis reaction, the process comprising:
   contacting a mixture of hydrogen gas and the gaseous carbon oxide and an olefin co-feed with a supported cobalt-manganese Fischer-Tropsch synthesis catalyst to provide the product composition;
   wherein the olefin co-feed comprises at least one $C_2$-$C_{14}$ olefin and is present in an amount in the range of 0.001 wt % to 40 wt % relative to the total amount of hydrogen, the gaseous carbon oxide and olefin;
   wherein a weight ratio of manganese to cobalt in the catalyst is at least 0.05 on an elemental basis; and
   wherein the molar ratio of hydrogen to the gaseous carbon oxide in the mixture of hydrogen and the gaseous carbon oxide is at least 0.5.

2. The process of claim 1, wherein the weight ratio of manganese to cobalt present in the synthesis catalyst is in the range of 0.05 to 3.0 on an elemental basis.

3. The process of claim 1, wherein the synthesis catalyst comprises at least 0.5 wt % manganese on an elemental basis.

4. The process of claim 1, wherein the synthesis catalyst comprises in the range of 2.5-25 wt % manganese on an elemental basis.

5. The process of claim 1, wherein the synthesis catalyst comprises cobalt in an amount of 2-35 wt %, on an elemental basis.

6. The process of claim 1, wherein the synthesis catalyst comprises cobalt in an amount of 5-20 wt %, on an elemental basis.

7. The process of claim 1, wherein the total amount of cobalt and manganese in the synthesis catalyst is no more than 40 wt % on an elemental basis, based on the total weight of the synthesis catalyst.

8. The process of claim 1, wherein the catalyst comprises a support material that comprises at least one oxide selected from alumina, zirconia, zinc oxide, ceria, silica and titania.

9. The process of claim 1, wherein the contacting is conducted at a pressure in the range of 1.0 to 10.0 MPa absolute.

10. The process of claim 1, wherein the contacting is conducted at a temperature of no more than 350° C.

11. The process of claim 1, wherein the gaseous carbon oxide is carbon monoxide.

12. The process of claim 1, wherein the gaseous carbon oxide is carbon dioxide or a mixture of carbon monoxide and carbon dioxide.

13. The process of claim 1, wherein the olefin co-feed is present in an amount in the range of 0.001 wt % to 30 wt %, relative to the total amount of hydrogen, the gaseous carbon oxide and olefin.

14. The process of claim 1, wherein the olefin co-feed is present in an amount in the range of 0.1 wt % to 20 wt %, relative to the total amount of hydrogen, the gaseous carbon oxide and olefin.

15. The process of claim 1, wherein the olefin co-feed comprises at least one linear olefin.

16. The process of claim 1, wherein the olefin co-feed comprises at least one cyclic olefin or at least one branched olefin.

17. The process of claim 1, wherein the olefin co-feed is at least 90% $C_2$-$C_{14}$ olefins.

18. The process of claim 1, wherein the olefin co-feed is at least 90% $C_2$-$C_5$ olefins.

19. The process of claim 1, wherein the product composition comprises at least 10 wt % alcohols.

20. The process of claim 1, wherein the product composition comprises at least 20 wt % alcohols.

\*    \*    \*    \*    \*